United States Patent
Gorden et al.

(10) Patent No.: US 10,166,289 B2
(45) Date of Patent: *Jan. 1, 2019

(54) COMPOSITIONS INCLUDING BETA-GLUCANS AND METHOD OF USE

(71) Applicant: BIOTHERA, INC., Eagan, MN (US)

(72) Inventors: Keith B. Gorden, Woodbury, MN (US); Nandita Bose, Plymouth, MN (US); Anissa S. H. Chan, Arden Hills, MN (US); William J. Grossman, Third Lake, IL (US)

(73) Assignee: Biothera, Inc., Eagan, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/609,853

(22) Filed: May 31, 2017

(65) Prior Publication Data

US 2017/0266279 A1  Sep. 21, 2017

Related U.S. Application Data

(63) Continuation of application No. 14/343,655, filed as application No. PCT/US2012/054071 on Sep. 7, 2012, now Pat. No. 9,694,070.

(60) Provisional application No. 61/532,647, filed on Sep. 9, 2011.

(51) Int. Cl.
| | | |
|---|---|---|
| *A61K 31/716* | (2006.01) | |
| *A61K 39/39* | (2006.01) | |
| *A61K 31/4738* | (2006.01) | |
| *A61K 31/7084* | (2006.01) | |
| *A61K 39/00* | (2006.01) | |

(52) U.S. Cl.
CPC .......... *A61K 39/39* (2013.01); *A61K 31/4738* (2013.01); *A61K 31/7084* (2013.01); *A61K 31/716* (2013.01); *A61K 2039/55511* (2013.01); *A61K 2039/55561* (2013.01); *A61K 2039/55572* (2013.01); *A61K 2039/55583* (2013.01)

(58) Field of Classification Search
None
See application file for complete search history.

(56) References Cited

U.S. PATENT DOCUMENTS

| 6,084,092 | A | 7/2000 | Wakshull et al. |
|---|---|---|---|
| 6,143,883 | A | 11/2000 | Lehmann et al. |
| 2004/0127458 | A1 | 7/2004 | Hunter et al. |
| 2008/0160089 | A1 | 7/2008 | Vitiello et al. |
| 2008/0167268 | A1 | 7/2008 | Yan |

FOREIGN PATENT DOCUMENTS

| JP | 2009-242367 A | 10/2009 |
|---|---|---|
| WO | WO 2006/119395 A2 | 11/2006 |
| WO | WO 2012/154680 A2 | 11/2012 |
| WO | WO 2012167061 A1 | 12/2012 |

OTHER PUBLICATIONS

PCT Patent Application No. PCT/US2012/054071, filed Sep. 7, 2012; International Preliminary Report on Patentability dated Mar. 20, 2014. 9 pages.
PCT Patent Application No. PCT/US12/54071, filed Sep. 7, 2012; International Search Report/Written Opinion dated Nov. 19, 2012. 13 pages.
European Patent Application No. 12829310.7, filed Sep. 7, 2012; Extended European Search Report dated Jan. 28, 2015, 9 pages.
European Patent Application No. 12 829 310, National Entry Date Apr. 8, 2014; Communication pursuant to Article 94(3) EPC dated Aug. 19, 2016, 9 pages.
Biothera, "Imprime PGG Boosts Immune Cell Function Without Inflammation," *Natural Products Insider*, Informa PLC, London, England. Aug. 15, 2005 [retrieved onlineAug. 7, 2015]. Retrieved from the Internet, <URL:http://www.naturalproductsinsider.com/articles/2005/08/imprime-pggtm-boosts-immune-cell-functionwithout-in.aspx>; 1 page.
Dalmo, Chapter 8, p. 95,"Immunostimulatory β(1,3)-D-glucans; prophylactic drugs against threatening infectious diseases of fish," *Bioactive Carbohydrate Polymers*, Paulsen (Ed.), Kluwer Academic Publishers, Dordrecht, the Netherlands, 2000.
Engstad, et al., "The effect of soluble β-1,3-glucan and lipopolysaccharide on cytokine production and coagulation activation in whole blood", 2002, *Int Immunopharmacol*, 2:1585-1597.
Frasnelli, et al., "TLR2 modulates inflammation in zymosan-induced arthritis in mice", Jan. 21, 2005, *Arthritis Res Ther*; 7:R370-379.
Fuentes, et al., "Laminarin, a soluble beta-glucan, inhibits macrophage phagocytosis of zymosan but has no. effect on lipopolysaccharide mediated augmentation of phagocytosis", Nov. 2011, *Int Immunopharmacol*, 11:1939-1945. Available online Aug. 19, 2011.
Goodridge, et al., "Activation of the innate immune receptor Dectin-1 upon formation of a 'phagocytic synapse'," *Nature*, Apr. 28, 2011; 472:471-476.
Harnack et al., "Oral administration of a soluble 1-3, 1-6 beta-glucan during prophylactic survivin peptide vaccination diminishes growth of a B cell lymphoma in mice," *International Immunopharmacology*, Oct. 2009; 9(11):1298-1303. Epub Aug. 4, 2009.

(Continued)

*Primary Examiner* — Brian Gangle
(74) *Attorney, Agent, or Firm* — Mueting, Raasch & Gebhardt, P.A.

(57) ABSTRACT

The invention generally relates to soluble beta-glucan compositions and method of using such compositions. In one aspect, an adjuvant for a pharmaceutical composition is described which includes a soluble beta-glucan and a TLR agonist, each in an amount that, in combination with the other, is effective to increase a subject's immune response to an antigen. In another aspect, compositions that generally include an antigen component, a soluble beta-glucan component, and a TLR agonist component and a method that generally includes administering to a subject a composition that comprises a soluble beta-glucan and a TLR agonist, each in an amount that, in combination with the other, is effective to increase a subject's immune response to an antigen, are described.

20 Claims, 4 Drawing Sheets

(56) References Cited

OTHER PUBLICATIONS

Hermanson, Chapter 2, "The Chemistry of Reactive Functional Groups," *Bioconjugate Techniques*, Academic Press, Waltham, Massachusetts; 1996. Cover page, publisher's page, and pp. 137-166.
Hermanson, Chapter 5, "Heterobifunctional Cross-Linkers," *Bioconjugate Techniques*, Academic Press, Waltham, Massachusetts; 1996. Cover page, publisher's page, and pp. 229-285.
Hida, et al., "Cell Wall β-Glucan Derived from *Candida albicans* Acts as a Trigger for Autoimmune Arthritis in SKG Mice", Aug. 2007, *Biol Pharm Bull*, 30(8):1589-1592. Available online Jun. 5, 2007.
Huang, et al., "Distinct Patterns of Dendritic Cell Cytokine Release Stimulated by Fungal β-Glucans and Toll-Like Receptor Agonists," *Infection and Immunity*, May 2009; 77(5):1774-1781.
Lai, et al., "Effects of dust and airborne dust components on antibody responses, body weight gain, and heart morphology of broilers," *Poultry Science*, Aug. 2009; 88:1838-1849.
Lee et al., "Purification of Soluble β-Glucan with Immune-enhancing Activity from the Cell Wall of Yeast," *Biosci Biotech Biochem*, 2001;65(4):837-841.
Li, et al., "Effects of β-glucan extracted from *Saccaromyces cerevisiae* on humoral and cellular immunity in weaned piglets," *Archives of Animal Nutrition*, Oct. 2005; 59(5):303-312.
Li, et al., "Orally Administered Particular β-Glucan Modulates Tumor-capturing Dendritic Cells and Improves Anti-tumor T Cell Responses in Cancer," *Clin Cancer Res.*, Nov. 2010; 16(21):5153-5164.
Ohno, et al., "Solublization of yeast cell-wall β-(1→3)-D-glucan by sodium hypochlorite oxidation and dimethyl sulfoxide extraction," *Carbohydrate Research*, 1999, 316:161-172.
Paulovicova et al., "Immunological properties of complex conjugates based on *Vibrio cholerae* 01 Ogawa lipopolysaccharide antigen," *Clin Exper Immunol*, 2006;144:521-527.
Peters et al., "Signals required for differentiating dendritic cells from human monocytes in vitro," *Advances in Experimental Medicine and Biology: Dendritic Cells in Fundamental and Clinical Immunology*, Kamperdijk, ed., Plenum Press, New York, 1993; 329:275-280.
"Scleroglucan" data sheet, Cargill, Incorporated, Minneapolis, Minnesota, 2005. 3 pages.
Selvaraj, et al., "Adjuvant and immunostimulatory effects of β-glucan administration in combination with lipopolysaccharide enhances survival and some immune parameters in carp challenged with *Aeromonas hydrophilia*," *Veterinary Immunology and Immunopathology*, Nov. 2006; 114(1-2):15-24.
Steinhagen et al., "TLR-based immune adjuvants," *Vaccine*, Apr. 12, 2011;29(17):3341-3355. Epub Aug. 14, 2010.
Tokunaka, et al., "Immunopharmacological and immunotoxicological activities of a water-soluble (1→3)-β-D-glucan, CSBG from *Candida* spp.," *International Journal of Immunopharmacology*, May 2000; 22(5):383-394.
Yan, "Particulate Yeast-derived Beta-Glucan Stimulates Anti-tumor T Cell Responses via Modulating Tumor Microenvironment toward Th1 Response," Meeting Abstract Supplement, *The FASEB Journal*, Mar. 2008, 22:1078.18-1078 [retrieved on Aug. 7, 2015]. Retrieved from the Internet, <URL:http://www.fasebj.org/cgi/content/meeting_abstract/22/1_MeetingAbstracts/1078.18>; 1 page.
Yanaki, et al. "Triple Helix of Scleroglucan in Dilute Aqueous Sodium Hydroxide," *Polymer Journal*, 1981; 13(12):1135-1143.
"Zymosan A" Product Information sheet, Sigma Product No. Z4250, Sigma, Sigma Aldrich Publications, St. Louis, Missouri, Mar. 18, 1998.
European Patent Application No. EP18162621.9 filed Mar. 19, 2018; Extended European Search Report dated May 5, 2018; 13 pages.
Liu et al., "Combined yeast-derived β-glucan with anti-tumor monoclonal antibody for cancer immunotherapy," *Experimental and Molecular Pathology*, Jun. 1, 2009; 86(3):208-214. Available online Jan. 21, 2009.

P1 = 67.3% Proliferating B-cells

P1 = 55.8% Proliferating B-cells

COMPOSITIONS INCLUDING BETA-GLUCANS AND METHOD OF USE

CROSS-REFERENCE TO RELATED APPLICATION

This application is a continuation application of U.S. patent application Ser. No. 14/343,655, pending, filed Jul. 3, 2014, which is a § 371 U.S. National Stage of International Application No. PCT/US2012/054071, filed Sep. 7, 2012, which claims priority to U.S. Provisional Patent Application Ser. No. 61/532,647, filed Sep. 9, 2011, each of which is incorporated by reference herein in its entirety.

SUMMARY OF THE INVENTION

The invention generally relates to soluble β-glucan compositions and method of using such compositions. In one aspect, we describe an adjuvant for a pharmaceutical composition. Generally, the adjuvant includes a soluble β-glucan and a TLR agonist, each in an amount that, in combination with the other, is effective to increase a subject's immune response to an antigen.

In another aspect, we describe compositions that generally include an antigen component, a soluble β-glucan component, and a TLR agonist component.

These compositions may be administered to a subject in order to modulate the subject's immune system. Thus, we further describe a method that generally includes administering to a subject a composition that comprises a soluble β-glucan and a TLR agonist, each in an amount that, in combination with the other, is effective to increase a subject's immune response to an antigen. In some cases, the antigen may be an additional component of the composition. In other cases, the antigen may be an endogenous antigen. Thus, in certain embodiments, we describe a method that generally includes administering to a subject an amount of soluble β-glucan effective to reduce chronic immune activation.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Compositions and methods related to combinations of soluble β-glucan and an agonist of a Toll-like receptor (TLR) are disclosed herein. The combinations can provide immunostimulatory activity when administered to a subject. Thus, the combination of a soluble β-glucan and a TLR agonist can be useful as an adjuvant to a therapeutic and/or prophylactic pharmaceutical composition—e.g., a vaccine—designed to induce an antigen-specific immune response. In some cases, the combination of a soluble β-glucan and a TLR agonist can provide increased immunostimulation and/or decreased side effects compared to the use of a TLR agonist as an adjuvant without the β-glucan.

Toll-like receptors (TLRs) are a class of proteins that recognize conserved components on microbes referred to as pathogen-associated molecular patterns (PAMPs). The interaction of PAMPs with their corresponding TLRs activates the innate immune response to process and present microbial antigens to cells of the adaptive immune system. Since their discovery in the 1990s, the TLRs have been shown to be involved in mammalian defense against pathogens and diseases related to microbial infections. Activating TLRs that are present on the surface of antigen presenting cells can induce a diverse range of effects including, for example, enhancing antigen processing and presentation. TLR recognition of the PAMPs isolated from their native pathogens can influence the body's response to foreign antigens. The TLR agonist properties of several PAMPS have been investigated in humans for a variety of purposes including, for example, as an adjuvant in tumor vaccines and viral vaccines. For example, imiquimod is a TLR 7/8 agonist that is useful for treating basal cell carcinoma, actinic keratosis, and genital warts. Monophosphoryl lipid A (MPL, a TLR 4 agonist) is used as an adjuvant in the HPV vaccine CERVARIX (GlaxoSmithKline). TLR agonists are currently being investigated in clinical trials mainly for their adjuvant properties in several disease indications (Steinhagen F, Kinjo T, Bode C, Klinman DM. TLR-based immune adjuvants. Vaccine. 2010 Aug. 14). Exemplary investigations are listed in Table 1.

TABLE 1

| TLR Agonists | Disease indications pursued in clinical trials |
|---|---|
| TLR 2-dependent adjuvants | Lyme disease, malaria, HIV, HBV, HPV |
| TLR 4-dependent adjuvants | Hepatitis B, genital HPV, genital HSV, EBV, leishmaniasis, HIV, malaria, tuberculosis, melanoma, breast cancer, lung cancer, prostate cancer |
| TLR 7/8-dependent adjuvants | CML, vulval cancer, prostate cancer, melanoma |
| TLR 9-dependent adjuvants | Infectious diseases: malaria, hepatitis B, influenza, anthrax Cancer: melanoma, breast cancer sarcoma, ovarian cancer, glioblastoma |

Yeast β-glucans are conserved microbial structures not found in mammalian cells. IMPRIME PGG (β(1,6)-[poly-1,3)-D-glucopyranosyl]-poly-β(1,3)-D-glucopyranose) is a soluble β-glucan isolated from yeast. Like many other soluble β-glucans, IMPRIME PGG is a conserved microbial structure not found in mammals. Because innate immune cells recognize IMPRIME PGG, IMPRIME PGG may be classified as a PAMP. Indeed, we have demonstrated that IMPRIME PGG, as well as other soluble β-glucans (i.e., laminarin), can bind to human neutrophils, monocytes, B-cells, and monocyte-derived dendritic cells (DCs). IMPRIME PGG binds various subsets of immune cells through complement binding receptors (CR2 on B-cells; CR3 on neutrophils and monocytes), not a TLR.

While many TLR-associated PAMPs (i.e., LPS, Pam3Cys, poly I:C) induce pro-inflammatory cytokines such as, for example, the NFκB-regulated cytokines TNF-α and IL-12, soluble β-glucans such as IMPRIME PGG do not appear to induce systemic pro-inflammatory cytokines. Thus, it appears that soluble β-glucan can modulate immune responses in a different manner than TLR agonists.

We have discovered that cells treated with soluble β-glucan can modulate the response to TLR agonists as measured by cellular activation markers and proliferation. This discovery may be exploited by combining a soluble β-glucan with a TLR agonist to produce an adjuvant composition that can enhance an immune response generated against a particular antigen. Because TLR agonists and soluble β-glucans modulate immune responses through different pathways, prior to this disclosure it was not clear whether, in combination with one another, the immunomodulatory activity of a soluble β-glucan would interfere with, complement, or have no effect on the immunomodulatory activity of the TLR agonist. We show that the soluble β-glucan can augment the immunomodulatory activity of a TLR agonist, thereby allowing one to achieve a desired level of immunomodulation using less TLR agonist. Certain benefits of this advance are discussed in more detail below.

In general, therefore, the compositions and methods described herein relate to improving the effectiveness of a pharmaceutical composition by increasing the immunostimulatory effect of the composition. Thus, for example, the compositions and methods described herein may be used to increase the immunological potency of a pharmaceutical composition such as, for example, a vaccine. Improving the effectiveness of a pharmaceutical composition can provide one or more benefits such as, for example, fewer administrations of the pharmaceutical composition to achieve a desired result, improving or establishing the efficacy of a pharmaceutical composition, faster or more complete treatment, reduced side effects associated with the pharmaceutical composition, or lower costs.

For example, certain vaccines include multiple immunogenic components, some of which (e.g., toxoids) may cause undesirable side effects such as, for example, pain, swelling, tenderness, and the like. The compositions and methods described herein may increase the immune response to a particular component of a pharmaceutical composition (e.g., a vaccine toxoid) sufficiently so that less of the particular component may be needed to provide the desired level of immune response, thereby reducing or even eliminating undesirable side effects of the component.

Since soluble β-glucans are macromolecules, their dissemination to the systemic circulation is much slower than, for example, small molecule TLR agonists. Their retention at the site of administration can create a localized area that is sensitized to TLR activation. This physical property can create a "depot effect" where antigen and immune cells are able to interact in the proper context for stimulating an immune response and enhancing the efficacy of a vaccine. This property would allow for a localized increase in expression of certain cytokines and chemokines (e.g., TNT-α, IL-12, IFN-α) while limiting the extent and/or likelihood that the immunostimulation may be manifested systemically. Thus, the combination of a TLR agonist with a soluble β-glucan can create a localized area of greater immunostimulation, thereby permitting the induction of a desired level of immunostimulation with, in some cases, a smaller amount of TLR agonist. Administering a smaller amount of TLR agonist can decrease the likelihood, extent, and/or effects of the TLR agonist inducing systemic inflammation Requiring less of each component of the pharmaceutical composition to achieve a desired immune response can result in lower costs to produce the pharmaceutical composition, such as when a particular component is costly to, for example, obtain or formulate.

Thus, in one aspect, we describe herein an adjuvant composition that generally includes a soluble β-glucan and a TLR agonist, each in an amount that, in combination with the other, is effective to increase a subject's immune response to an antigen.

The soluble β-glucan compound can be or be derived from, for example, β-glucan derived from a fungal yeast source such as, for example, *Saccharomyces cerevisiae, Torula (candida utilis), Candida albicans, Pichia stipitis*, or any other yeast source; β-glucan derived from another fungal source such as, for example, scleroglucan from *Sclerotium rofsii* or any other non-yeast fungal source; β-glucan from an algal source such as, for example, laminarin or phycarine from *Laminaria digitata* or any other algal source; β-glucan from a bacterial source such as, for example, curdlan from *Alcaligenes faecalis* or any other bacterial source; β-glucan from a mushroom source such as, for example, schizophyllan from *Schizophyllan commune*, lentinan from *Lentinan edodes*, grifolan from *Grifola frondosa*, ganoderan from *Ganoderma lucidum*, krestin from *Coriolus versicolor*, pachyman from *Poria cocos Wolf*, or any other mushroom source; β-glucan derived from a cereal grain source such as, for example, oat glucan, barley glucan, or any other cereal grain source; β-glucan derived from a lichen source such as, for example, pustulan from *Umbilicaris pustulata*, lichenan from *Cetraria islandica*, or any other lichen source.

In some embodiments, the β-glucan can be water-soluble. In some embodiments, the β-glucan may be or be derived from a *Saccharomyces cerevisiae* β-glucan. One such form of β-glucan derived from *Saccharomyces cerevisiae* is β(1,6)-[poly-1,3)-D-glucopyranosyl]-poly-b(1,3)-D-glucopyranose—also referred to herein as IMPRIME PGG, a water-soluble form of yeast-derived β-glucan. Laminarin is one example of a β-1,3/1,6 glucan derived from algae. In some embodiments, the soluble β-glucan may be opsonized as described in, for example, International Patent Application No. PCT/US2012/040435, filed Jun. 1, 2012.

The adjuvant composition further includes an agonist of at least one TLR. As used herein, "agonist" refers to a compound that can combine with a TLR to induce a TLR-mediated cellular activity. TLR-mediated cellular activities are described in more detail below. An agonist may be a ligand that directly binds to the receptor. Alternatively, an agonist may combine with a receptor indirectly by, for example, forming a complex with another molecule that directly binds to the TLR. An agonist may be referred to as an agonist of a particular TLR (e.g., a TLR 9 agonist) or a particular combination of TLRs (e.g., a TLR 7/8 agonist—an agonist of both TLR 7 and TLR 8). Exemplary TLR agonists include, for example, an agonist of TLR 1 (e.g., a triacyl lipopeptide), an agonist of TLR 2 (e.g. lipoteichoic acid), an agonist of TLR 3 (e.g., dsRNA), an agonist of TLR 4 (e.g., lipopolysaccharide, or LPS), an agonist of TLR 5 (e.g., flagellin), an agonist of TLR 6 (e.g., peptidoglycan), an agonist of TLR 7 (e.g., ssRNA, imidazoquinolines, loxoribine), an agonist of TLR 8 (e.g., imidazoquinolines, loxoribine), or an agonist of TLR 9 (e.g., an unmethylated CpG oligonucleotide).

In certain embodiments, the TLR agonist may be an agonist of one or both of TLR 7 and/or TLR 8. In other embodiments, the TLR agonist may be an agonist of TLR 9.

In some embodiments, the soluble β-glucan and the TLR agonist may be covalently bound to one another. Methods for covalently binding the soluble β-glucan and TLR agonist include methods for, for example, conjugating or crosslinking biological compounds and are known to those of ordinary skill in the art. Heterobifunctional cross-linkers are known and many are commercially available. See for example, Hermanson, G. (1996), *Bioconjugate Techniques*, Academic Press, Chapter 5 "Heterobifunctional Cross-Linkers", 229-285. Moreover, reactive groups of the soluble β-glucan and TLR agonist suitable for cross-linking sites can include reactive groups discussed in Hermanson, G. (1996), *Bioconjugate Techniques*, Academic Press, Chapter 2 "The Chemistry of Reactive Functional Groups", 137-166. Additionally, methods for derivatizing β-glucan compounds are described in, for example, International Patent Application No. PCT/US2012/036795.

The adjuvant composition includes soluble β-glucan and TLR agonist in amounts that, in combination with one another, are effective to induce an immune response against a target antigen. Components of such an adjuvant composition—or of a larger composition further including an antigen, as described in more detail below—may be said to be delivered "in combination" with one another if the components are provided in any manner that permits the biological effect of contacting one component with immune cells to be sustained at least until another component is contacted with the immune cells. Thus, components may be delivered in combination with one another even if they are provided in separate formulations, delivered via different routes of administration, and/or administered at different times. Generally, any multicomponent composition described herein may be provided in one or more separate formulations.

For example, a soluble β-glucan and a TLR agonist may be considered "in combination" with one another regardless of whether the components are provided in a single formulation or the soluble β-glucan is administered in one formulation and the TLR agonist is administered in a second formulation. When administered in different formulations, the components may be administered at different times, if desired, but administered so that the immune response induced is greater than the immune response induced if either the soluble β-glucan or the TLR agonist is administered alone.

Also as used herein, the team "induce" and variations thereof refer to any measurable increase in cellular activity. For example, induction of a TLR-mediated cellular activity may include, for example, activation, proliferation, or maturation of a population of immune cells, increasing the production of a cytokine, and/or another indicator of increased immune function. In certain embodiments, induction of an immune response can include increasing the proliferation of B cells, producing antigen-specific antibodies, increasing the proliferation of antigen-specific T cells, improving dendritic cell antigen presentation and/or an increasing expression of certain cytokines, chemokines and co-stimulatory markers.

Figure 2:
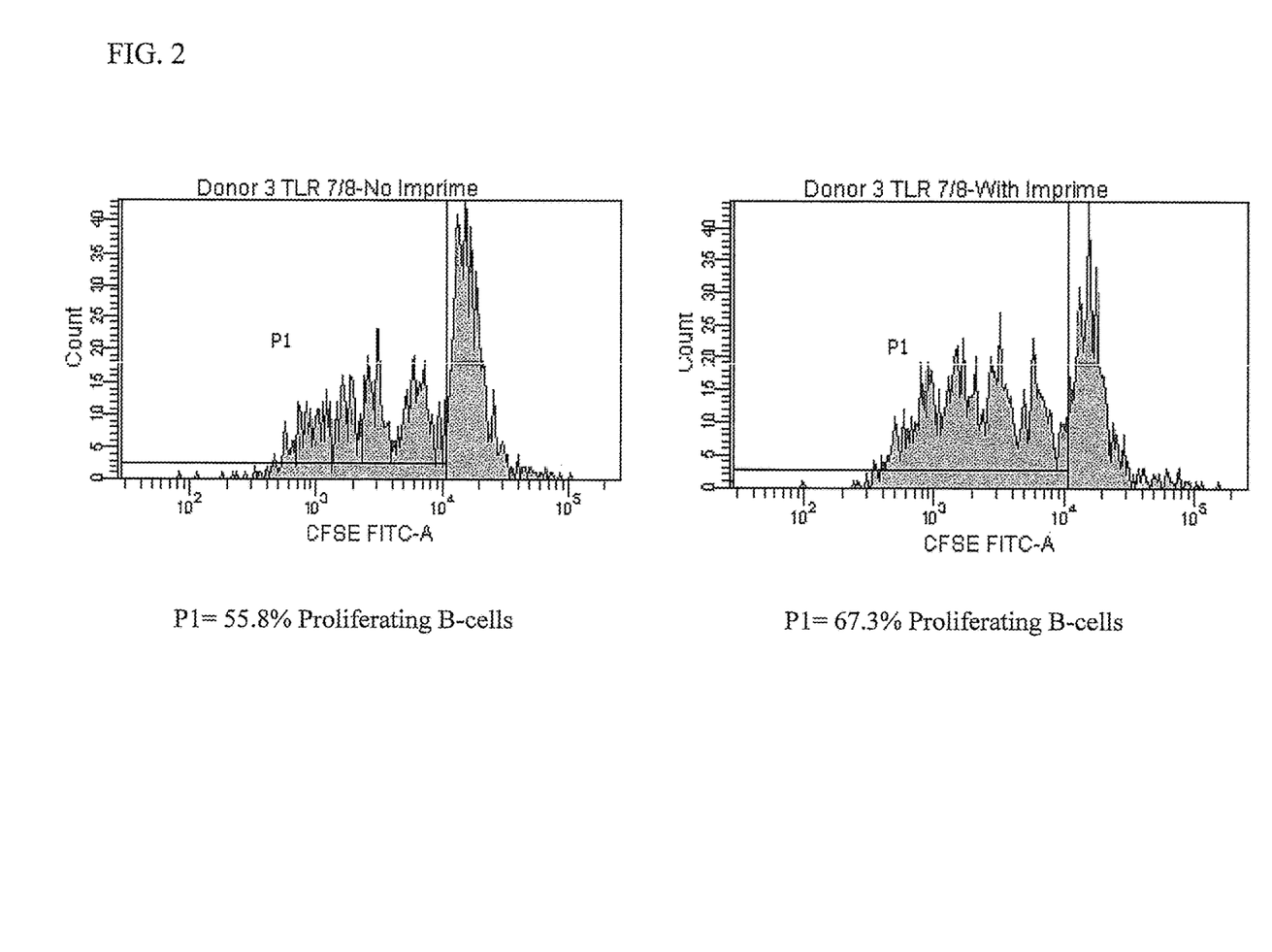
FIG. 2 shows soluble β-glucan modulation of TLR agonist-induced B cell proliferation.
Figure 3:
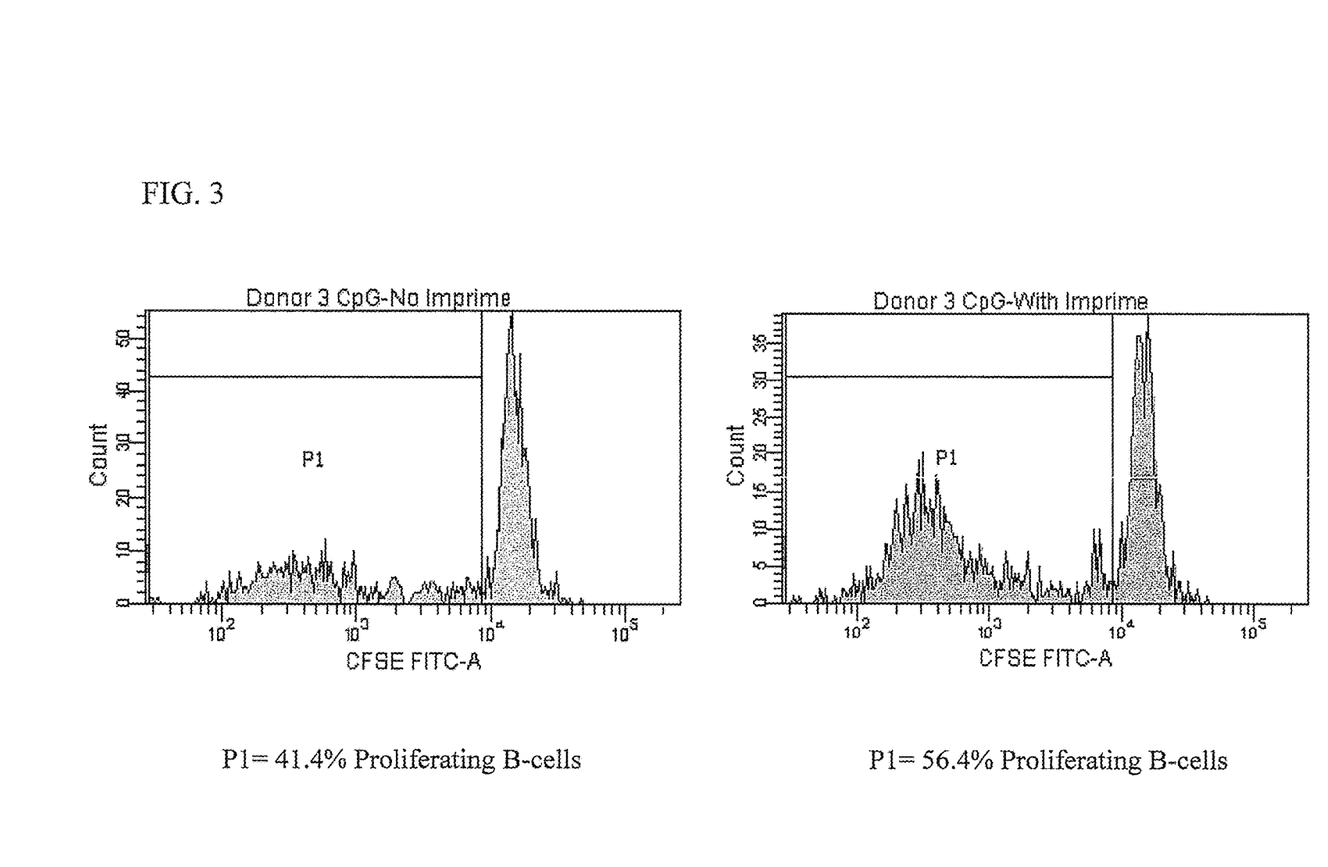
FIG. 3 shows soluble β-glucan modulation of TLR agonist-induced B cell proliferation.
Figure 4:
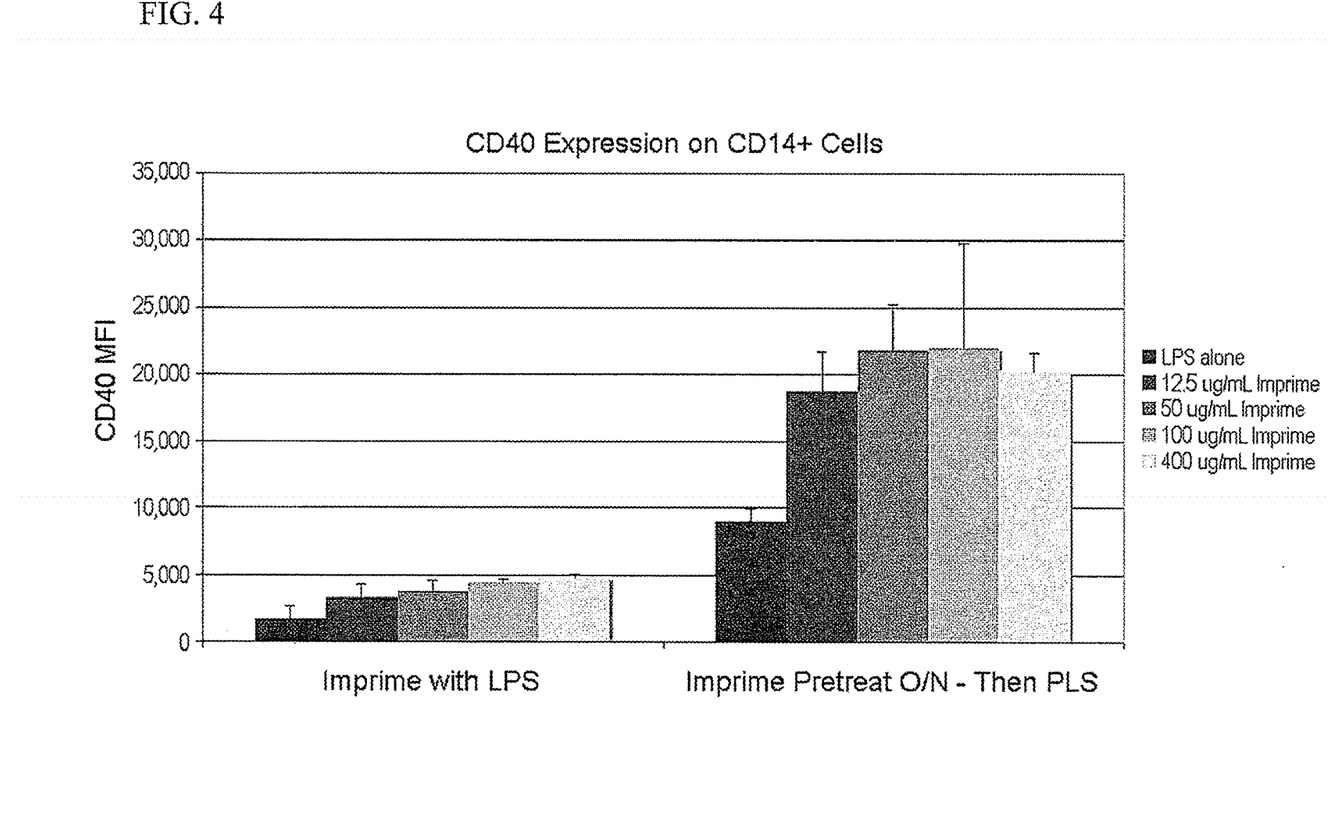
FIG. 4 shows soluble β-glucan modulation of TLR-induced co-stimulatory marker expression by monocytes.

For example, FIG. 2 and FIG. 3 show that treating peripheral blood mononuclear cells (PBMCs) with a soluble β-glucan, IMPRIME PGG, and either a TLR 7/8 agonist (CL097, FIG. 2) or a TLR 9 agonist (CpG 2006, FIG. 3) increases B cell proliferation compared to PBMCs treated with only the TLR agonist. FIG. 4 shows an increase in CD40 expression when PBMCs are incubated with a soluble β-glucan, IMPRIME PGG, and a TLR 4 agonist, LPS, compared to treating the PBMCs with only the TLR agonist. This effect is magnified when the PBMCs are pre-incubated with the soluble β-glucan before being treated with the TLR agonist.

The activities exemplified in FIGS. 2-4 are fully indicative of a more general phenomenon manifested when soluble β-glucan and a TLR agonist are combined. Thus, a person of ordinary skill in the art can extrapolate the activation exemplified in FIGS. 2-4 to other manifestations of immunomodulation such as, for example, increasing proliferation of antigen-specific T cells, producing antigen-specific antibodies, and, ultimately, prophylactic and/or therapeutic treatment of neoplastic and/or infectious conditions.

The antigen against which the immune response is induced may be an endogenous antigen such as, for example, a tumor antigen associated with a tumor already present in the subject. In other instances, the antigen may be an exogenous antigen such as, for example, an antigen present in a therapeutic or prophylactic vaccine.

In the case of exogenous antigens, the antigen may be included in the soluble β-glucan/TLR agonist composition or provided in a separate composition. Thus, in certain embodiments, compositions described herein can generally include an antigen component, a soluble β-glucan component, and a TLR agonist component.

As used herein, "antigen" and variations thereof refer to any material capable of raising an immune response in a subject challenged with the material. In various embodiments, an antigen may raise a cell-mediated immune response, a humoral immune response, or both. Exemplary antigens include but are not limited to peptides or polypeptides; lipids; glycolipids; polysaccharides; carbohydrates; polynucleotides; prions; live or inactivated bacteria, viruses, fungi, or parasites; and bacterial, viral, fungal, protozoal, tumor-derived, or organism-derived immunogens, toxins or toxoids.

Thus, exemplary antigens include viral antigens such as, for example, antigens associated with influenza, Hepatitis A, Hepatitis B, Hepatitis C, adenovirus, Herpes Simplex B, or other suitable virus.

Exemplary antigens also can include an antigen associated with a particular type of neoplasm or tumor. Such antigens include, for example, MUC-1, CA 125, telomerase/hTERT, PSA, NY-ESO-1, MAGE, AML1 fusions, EGFR, HER2/NEU, gp100, WT1, CEA, or other antigen having a known association with one or more tumors.

Exemplary antigens also can include bacterial antigens such as, for example, tetanus toxoid, diphtheria toxoid, a *Staphylococcus* spp. antigen, a *Pneumococcus* spp. antigen, a *Klebsiella* spp. antigen, or another bacterial antigen.

Exemplary antigens also can include parasitic antigens such as, for example, a *Trypanosoma* spp. antigen, a *Toxoplasma* spp. antigen, a *Leishmania* spp. antigen, a *Plasmodium* spp. antigen, a *Schistosoma* spp. antigen, or another parasitic antigen.

The adjuvant composition includes soluble β-glucan and TLR agonist in amounts that, in combination with one another, are effective to induce an immune response against a target antigen. In some embodiments, administering the adjuvant composition can provide prophylactic and/or therapeutic treatment for a condition. As used herein, "treat," "treatment" or variations thereof refer to reducing, limiting progression, ameliorating, preventing, or resolving, to any extent, the symptoms or clinical signs related to a condition. As used herein, "ameliorate" refers to any reduction in the extent, severity, frequency, and/or likelihood of a symptom or clinical sign characteristic of a particular condition. Treatment may be prophylactic or therapeutic. "Prophylactic" and variations thereof refer to a treatment that limits, to any extent, the development and/or appearance of a symptom or clinical sign of a condition. "Therapeutic" and variations thereof refer to a treatment that ameliorates one or more existing symptoms or clinical signs associated with a condition. As used herein, "symptom" refers to any subjective evidence of disease or of a patient's condition, and "sign" or "clinical sign" refers to an objective physical finding relating to a particular condition capable of being found by one other than the patient.

Generally, cells associated with a condition—e.g., tumor cells or cells of a pathogen—express certain antigen so that an immune response generated against the antigen can be effective for inactivating and/or eliminating at least some of the cells associated with the condition. Thus, administering the adjuvant composition can promote an immune response against cells that express the antigen, limit progression of the condition, and/or ameliorate one or more symptoms or clinical signs of the condition.

Certain TLR agonists can induce an increased immune response against an antigen, but may do so with concomitant side effects such as, for example, the systemic induction of certain pro-inflammatory cytokines such as, for example, Type I interferons, TNF-α, IL-1, IL-6, IL-8, IL-10, IL-12, MIP-1, and/or MCP-1. Because β-glucans induce immune responses through a non-inflammatory pathway, the combination of a TLR agonist and a β-glucan can induce a desired level of immune response while decreasing the amount of the TLR agonist being administered and, therefore, decrease the likelihood and/or extent of inflammation associated with the TLR agonist-induced immune response.

Consequently, the adjuvants compositions described herein may have particular utility in connection with treatment of individuals having chronic immune activation as may be associated with conditions such as, for example, atherosclerosis or other autoimmunity-associated disorders.

Atherosclerosis is a condition in which an artery wall thickens as a result of the accumulation of fatty materials such as cholesterol. It is a syndrome characterized by a chronic inflammatory response in the walls of arteries. More generally, autoimmunity disorders involve the failure of an organism to recognize its own constituent parts as self, which allows an immune response against its own cells and tissues. Exemplary autoimmune conditions include, for example, Celiac disease, diabetes mellitus type 1 (IDDM), systemic lupus erythematosus (SLE), Sjögren's syndrome, Churg-Strauss Syndrome, Hashimoto's thyroiditis, Graves' disease, idiopathic thrombocytopenic purpura, rheumatoid arthritis (RA), lupus, and allergies.

The adjuvant compositions described herein also can be useful for providing reduced-inflammation treatment of a primary neoplastic condition—e.g., a tumor—or a primary infectious condition in individuals having a secondary autoimmune condition, individuals for whom the induction of inflammation may aggravate the autoimmune condition and reduce the efficacy and/or compliance of treatment for the primary condition. Such treatment may be effective to ameliorate the primary condition with reduced aggravation of the autoimmune condition compared to the inflammatory aggravation one may observe using, for example, only a TLR agonist as an adjuvant in the treatment of the primary condition.

The adjuvant composition may be provided in a formulation along with a "carrier." As noted above, the components of the adjuvant composition may be provided in a single formulation or in separate formulation, both with respect to each other and with respect to any additional component such as, for example, an antigen. In the description that follows, any reference to "the adjuvant composition" expressly contemplates that the adjuvant composition may be provided in one or more formulations.

As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the soluble β-glucan or the TLR agonist, its use in the therapeutic compositions is contemplated. Supplementary active ingredients also can be incorporated into the compositions.

By "pharmaceutically acceptable" is meant a material that is not biologically or otherwise undesirable, i.e., the material may be administered to an individual along with soluble β-glucan and/or a TLR agonist without causing any undesirable biological effects or interacting in a deleterious manner with any of the other components of the pharmaceutical composition in which it is contained.

The soluble β-glucan and TLR agonist may be provided in a single formulation or in separate formulations. A formulation may be adapted to a preferred route of administration. Thus, a formulation can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). It is foreseen that a formulation can be administered to a mucosal surface, such as by administration to, for example, the nasal or respiratory mucosa (e.g., by spray or aerosol). A formulation also can be administered via a sustained or delayed release.

A formulation may be conveniently presented in unit dosage form and may be prepared by methods well known in the art of pharmacy. Methods of preparing a formulation with a pharmaceutically acceptable carrier include the step of bringing the soluble β-glucan and/or the TLR agonist into association with a carrier that constitutes one or more accessory ingredients. In general, a formulation may be prepared by uniformly and/or intimately bringing the soluble β-glucan and/or the TLR agonist into association with a liquid carrier, a finely divided solid carrier, or both, and then, if necessary, shaping the product into the desired formulations.

The adjuvant composition including the soluble β-glucan and the TLR agonist may be provided in any suitable form including but not limited to a solution, a suspension, an emulsion, a spray, an aerosol, or any form of mixture. The adjuvant composition may be delivered in formulation with any pharmaceutically acceptable excipient, carrier, or vehicle. For example, the adjuvant composition may be delivered in a conventional topical dosage form such as, for example, a cream, an ointment, an aerosol formulation, a non-aerosol spray, a gel, a lotion, and the like. A formulation may further include one or more additives including such as, for example, an adjuvant, a skin penetration enhancer, a colorant, a fragrance, a flavoring, a moisturizer, a thickener, and the like.

In another aspect, the invention provides methods that generally involve administering to an individual an effective amount of the adjuvant composition to induce an immune response against one or more predetermined antigens.

The amount of the adjuvant composition effective to induce one or more of the desired effects can vary depending on various factors including, but not limited to, the particular TLR agonist in the adjuvant composition, the weight, physical condition, and/or age of the subject, and/or the route of administration. Accordingly, it is not practical to set forth generally the amount of adjuvant composition, or the relative amounts of each component of the adjuvant composition, that constitutes an effective amount for all possible applications. Those of ordinary skill in the art, however, can readily determine the appropriate amount with due consideration of such factors.

In some embodiments, the method can include administering sufficient adjuvant composition to provide a dose of, for example, from about 100 ng/kg to about 50 mg/kg of each of the soluble β-glucan and the TLR agonist to the subject, although in some embodiments the methods may be performed by administering the adjuvant composition in a dose outside this range. In some embodiments, the method includes administering sufficient adjuvant composition to provide a dose of each component of the adjuvant composition of from about 10 μg/kg to about 5 mg/kg to the subject, for example, a dose of each component of from about 100 μg/kg to about 1 mg/kg.

Alternatively, the dose may be calculated using actual body weight obtained just prior to the beginning of a treatment course. For the dosages calculated in this way, body surface area (m²) is calculated prior to the beginning of the treatment course using the Dubois method: $m^2=(wt\ kg^{0.425} \times height\ cm^{0.725}) \times 0.007184$. In some embodiments, therefore, the method can include administering sufficient amounts of the adjuvant composition to provide a dose of each component of the adjuvant composition of, for example, from about 0.01 mg/m² to about 10 mg/m².

In embodiments in which an exogenous antigen is administered in combination with the adjuvant composition, the antigen may be administered in one or more separate "priming" doses prior to administering the antigen in combination with the adjuvant composition. Priming in this way may provide an increased immune response upon administration of the antigen in combination with the adjuvant composition. In other embodiments, the antigen may be administered in one or more separate "booster" doses after administering the antigen in combination with the adjuvant composition. Boosting in this way may reinvigorate an at least partially resolved immune response by activating $CD8^+$ memory T cells, $CD4^+$ memory T cells, or both. In still other embodiments, the adjuvant composition may be administered in one or more separate booster doses after administering the antigen in combination with the adjuvant composition. The adjuvant composition provided in a booster dose may be the same or different than the adjuvant composition provided in combination with the antigen, and may be the same or different than the adjuvant composition provided in any other booster dose.

EXAMPLES

Example 1

Figure 1:
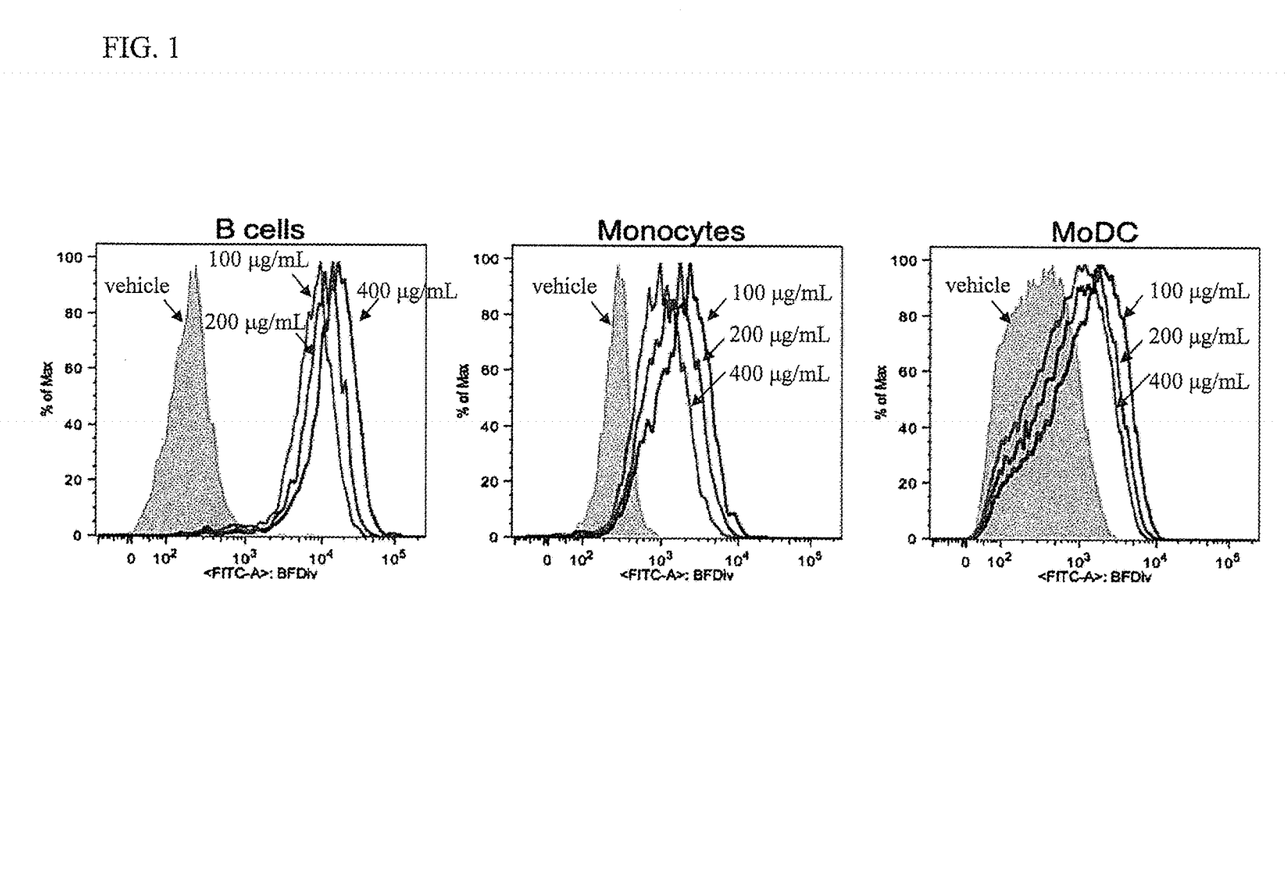
FIG. 1 shows binding of soluble β-glucan to B cells, monocytes, or monocyte-derived dendritic cells.

Monocyte-derived dendritic cells (MoDCs) were prepared from blood obtained from healthy volunteers as described in Peters et al. (Advances in Experimental Medicine and Biology; 329:275-280; 1993). At day 7, the MoDCs were resuspended in RPMI 1640 supplemented with 10% human serum (Sigma-Aldrich, St. Louis, Mo.). PBMCs were obtained from healthy volunteers and similarly resuspended in RPMI 1640 supplemented with 10% human serum. The MoDCs and PBMCs were treated with vehicle alone or with IMPRIME (Biothera, Eagan, Minn.) at 100 μg/mL, 200 μg/mL, or 400 μg/mL for two hours. Binding of IMPRIME was assessed by flow cytometric analysis with a glucan specific Ab BFD IV (U.S. Pat. No. 6,084,092).

Results are shown in FIG. 1

Example 2

TLR activation of B cells induces cellular proliferation that can be measured by a reduction in the staining intensity of the intracellular dye, carboxyfluorescein succinimidyl ester (CFSE, Invitrogen, Life Technologies Corp., Carlsbad, Calif.). The principle behind this technique is that as a cell divides the CFSE dye is diluted in half between the daughter cells after each division. The reduction in the staining intensity measured by FACS analysis (BD Biosciences, San Jose, Calif.) indicates that proliferation has occurred and can be monitored over several passages.

a) Modulation of TLR 7/8 agonist imidazoquinoline CL097

PBMCs obtained from healthy volunteers were treated with 2 μM CL097 (InvivoGen, San Diego, Calif.) in the presence or absence of 50 μg/mL IMPRIME PGG (Biothera, Eagan, Minn.) and cultured over five days in media containing 10% fresh human serum (Sigma-Aldrich, St. Louis, Mo.). The cells were stained with an anti-CD19 antibody (BioLegend, Inc., San Diego, Calif.) to identify the B cell subset in the PBMC mixture and intensity of CFSE staining was measured my FACS analysis (BD Biosciences, San Jose, Calif.).

Results are shown in FIG. 2.

b) Modulation of TLR-9 agonist CpG 2006

PBMCs obtained from healthy volunteers were treated with 100 nM CpG 2006 (InvivoGen, San Diego, Calif.) in the presence or absence of 50 μg/mL IMPRIME PGG (Biothera, Eagan, Minn.) and cultured over five days in media containing 10% fresh human serum (Sigma-Aldrich, St. Louis, Mo.). The cells were stained with an anti-CD19 antibody (BioLegend, Inc., San Diego, Calif.) to identify the B cell subset in the PBMC mixture and intensity of CFSE staining was measured my FACS analysis (BD Biosciences, San Jose, Calif.).

Results are shown in FIG. 3.

Example 3

PBMCs obtained from healthy volunteers were treated with 25 ng/mL LPS (InvivoGen, San Diego, Calif.) either concurrently with noted doses of IMPRIME PGG (Biothera, Eagan, Minn.) or after cells were pretreated overnight with IMPRIME PGG. The cells were cultured over five days in media containing 10% fresh human serum and then stained with an anti-CD14 antibody (BioLegend, Inc., San Diego, Calif.) to identify the monocyte subset in the PBMC mixture and an anti-CD40 antibody (BioLegend, Inc., San Diego, Calif.) to evaluate CD40 expression by FACS analysis (BD Biosciences, San Jose, Calif.).

Results are shown in FIG. 4.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

As used herein, the term "and/or" means one or all of the listed elements or a combination of any two or more of the listed elements; the term "comprises" and variations thereof do not have a limiting meaning where these terms appear in the description and claims; unless specifically stated otherwise, "a," "an," "the," and "at least one" are used interchangeably and mean one or more than one; and recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method comprising:
   administering to a subject a first composition that comprises a yeast-derived soluble β-glucan; and
   administering to the subject a second composition that comprises a TLR agonist component, which is administered subsequent to the first composition;
   wherein each of the first composition and second composition is in an amount that, in combination with the other, is effective to increase the subject's immune response to an antigen.

2. The method of claim 1 wherein the second composition comprises one or more of TLR 2, TLR 3, TLR 4, TLR 5, TLR 6, TLR 7, TLR 8 or TLR 9.

3. The method of claim 1 wherein the first composition and second composition induce a TLR-induced immune response greater than the TLR-induced immune response induced by administering the TLR agonist component without the yeast-derived soluble β-glucan.

4. The method of claim 1 wherein the first composition and second composition induce a predetermined level of a TLR agonist-dependent immune response using less TLR agonist component than is necessary to induce the predetermined level if the TLR agonist component is administered without the yeast-derived soluble β-glucan.

5. The method of claim 1 wherein TLR-dependent side effects are reduced for a predetermined level of TLR-dependent immune response compared to the TLR-dependent side effects observed if the TLR agonist component is administered without the yeast-derived soluble β-glucan.

6. The method of claim 3 wherein the TLR-induced immune response comprises B-cell proliferation.

7. The method of claim 3 wherein the TLR-induced immune response comprises proliferation of antigen-specific T-cells.

8. The method of claim 3 wherein the TLR-induced immune response comprises co-stimulatory marker expression.

9. The method of claim 1 wherein the antigen comprises a vaccine antigen.

10. The method of claim 1 wherein the antigen comprises a tumor antigen.

11. The method of claim 1 wherein the antigen comprises an antigen from an infectious pathogen.

12. The method of claim 11 wherein the infectious pathogen comprises a bacterium, a virus, a parasite, or a fungus.

13. The method of claim 1 wherein the second composition is administered a day following administration of the first composition.

14. A method comprising:
    administering to a subject on a first day, a first composition that comprises a yeast-derived soluble β-glucan; and
    administering to the subject on a second day, a second composition that comprises a TLR agonist component;
    wherein each of the first composition and second composition is in an amount that, in combination with the other, is effective to increase the subject's immune response to an antigen.

15. The method of claim 14 wherein the second composition comprises one or more of TLR 2, TLR 3, TLR 4, TLR 5, TLR 6, TLR 7, TLR 8 or TLR 9.

16. The method of claim 14 wherein the antigen comprises a vaccine antigen.

17. The method of claim 14 wherein the antigen comprises a tumor antigen.

18. The method of claim 14 wherein the antigen comprises an antigen from an infectious pathogen.

19. The method of claim 18 wherein the infectious pathogen comprises a bacterium, a virus, a parasite, or a fungus.

20. The method of claim 14 wherein the yeast-derived soluble β-glucan comprises β(1,6)-[poly-1,3)-D-glucopyranosyl]-poly-β(1,3)-D-glucopyranose.

* * * * *